(12) United States Patent
Jugl et al.

(10) Patent No.: US 10,973,981 B2
(45) Date of Patent: Apr. 13, 2021

(54) MEDICAL DEVICE WITH IMPACT RESISTANT HOUSING

(71) Applicant: Sanofi-Aventis Deutschland GmbH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 559 days.

(21) Appl. No.: 14/424,298

(22) PCT Filed: Aug. 28, 2013

(86) PCT No.: PCT/EP2013/067751
§ 371 (c)(1),
(2) Date: Feb. 26, 2015

(87) PCT Pub. No.: WO2014/033141
PCT Pub. Date: Mar. 6, 2014

(65) Prior Publication Data
US 2015/0224262 A1 Aug. 13, 2015

(30) Foreign Application Priority Data

Aug. 31, 2012 (EP) .................................... 12182523

(51) Int. Cl.
*A61M 5/31* (2006.01)
*A61M 5/142* (2006.01)
(Continued)

(52) U.S. Cl.
CPC ........... *A61M 5/31* (2013.01); *A61B 5/14532* (2013.01); *A61M 5/14244* (2013.01);
(Continued)

(58) Field of Classification Search
CPC .... A61M 5/14244; A61M 2005/14264; A61M 2205/0216; A61M 5/002; A61M 5/008; A61M 5/31; A61M 5/20; A61M 2005/2418; A61M 2005/1416; A61M 2205/0238; A61M 2207/00; A61M 25/0013; A61M 25/00; A61M 25/0052; A61M 25/0074; A61M 25/008; A61M 25/0054;
(Continued)

(56) References Cited

U.S. PATENT DOCUMENTS 5,695,090 A * 12/1997 Burdick .................. A61J 1/165
206/521
5,860,556 A 1/1999 Robbins, III
(Continued)

FOREIGN PATENT DOCUMENTS

EP 1952835 A1 8/2008
JP H7-211690 A 8/1995
(Continued)

*Primary Examiner* — Tiffany Legette
*Assistant Examiner* — Alexandra Lalonde
(74) *Attorney, Agent, or Firm* — McCarter & English, LLP

(57) ABSTRACT

The present invention relates to a housing of a medical device and to a respective medical device, wherein the housing comprises a body to receive at least one device component and wherein the body is flexibly deformable in response to mechanical impact above a predefined threshold.

15 Claims, 2 Drawing Sheets

Specification includes a Sequence Listing.

(51) Int. Cl.
*A61M 5/24* (2006.01)
*A61B 5/145* (2006.01)
*B29C 65/70* (2006.01)
*B29D 22/00* (2006.01)
*B29L 31/00* (2006.01)

(52) U.S. Cl.
CPC ............... *A61M 5/24* (2013.01); *B29C 65/70* (2013.01); *B29D 22/00* (2013.01); *A61B 2562/164* (2013.01); *A61M 2005/14264* (2013.01); *A61M 2205/0216* (2013.01); *A61M 2207/00* (2013.01); *A61M 2230/201* (2013.01); *B29L 2031/753* (2013.01)

(58) Field of Classification Search
CPC .. A61M 25/0043; A61M 1/167; A61M 1/308; A61M 1/3636; A61M 2230/63; A61M 25/0053; A61M 2025/09133; A61M 5/24; A61M 2005/2403; A61M 2005/2407; A61M 2005/2411; A61M 2005/2414; B29C 45/1676; B29C 65/70; A61B 2050/311; G01N 33/48778; B29L 2031/7544; B29L 2031/753; A61N 1/375
See application file for complete search history.

(56) References Cited

U.S. PATENT DOCUMENTS

| | | | |
|---|---|---|---|
| 5,913,448 A | 6/1999 | Mann et al. | |
| 6,315,151 B1 | 11/2001 | Hupp et al. | |
| 6,532,152 B1 | 3/2003 | White et al. | |
| 6,582,408 B1* | 6/2003 | Buch-Rasmussen | A61M 5/24 604/232 |
| 2003/0120320 A1* | 6/2003 | Solom | A61N 1/375 607/36 |
| 2004/0243102 A1* | 12/2004 | Berg | A61M 25/0054 604/525 |
| 2007/0135830 A1* | 6/2007 | Schaeffer | A61M 25/0074 606/192 |
| 2007/0151882 A1* | 7/2007 | Cocheteux | A61M 5/008 206/366 |
| 2007/0185450 A1 | 8/2007 | De Polo et al. | |
| 2008/0183133 A1 | 7/2008 | Kiersh | |
| 2011/0092905 A1* | 4/2011 | Cowe | A61M 5/20 604/135 |
| 2011/0154889 A1* | 6/2011 | Stafford | B29C 45/16 73/61.59 |
| 2011/0202005 A1* | 8/2011 | Yodfat | A61M 5/1413 604/151 |
| 2012/0123338 A1* | 5/2012 | Rouleau | A61M 5/14244 604/151 |

FOREIGN PATENT DOCUMENTS

| | | |
|---|---|---|
| JP | H08-57046 A | 3/1996 |
| JP | 2003-245347 A | 9/2003 |
| JP | 2007-16918 A | 1/2007 |
| JP | 2007-296374 A | 11/2007 |
| JP | 2008-156925 A | 1/2008 |
| JP | 2011-5182 A | 1/2011 |
| WO | 94/24002 A1 | 10/1994 |
| WO | 98/29315 A1 | 7/1998 |
| WO | 98/45191 A1 | 10/1998 |
| WO | 9965547 A1 | 12/1999 |
| WO | 2008077914 A2 | 7/2008 |
| WO | WO 2012081992 A2 * | 6/2012 ............... C09J 9/02 |

* cited by examiner

MEDICAL DEVICE WITH IMPACT RESISTANT HOUSING

CROSS REFERENCE TO RELATED APPLICATIONS

The present application is a U.S. National Phase Application pursuant to 35 U.S.C. § 371 of International Application No. PCT/EP2013/067751 filed Aug. 28, 2013, which claims priority to European Patent Application No. 12182523.6 filed Aug. 31, 2012. The entire disclosure contents of these applications are herewith incorporated by reference into the present application.

SEQUENCE LISTING

The instant application contains a Sequence Listing which has been submitted electronically in ASCII format and is hereby incorporated by reference in its entirety. Said ASCII copy, created on Feb. 23, 2021, is named 128868_05802_SL.txt and is 29,399 bytes in size.

FIELD OF INVENTION

The present invention relates to the field of medical devices and in particular to a housing of a medical device providing an impact-absorbing functionality to protect the device and components thereof against mechanical impact.

BACKGROUND

There exists a variety of portable medical devices such like injection devices or analysis devices, by way of which a patient may conduct self-treatment, in particular self-administration of a medicament.

Especially with patients suffering diabetes, a blood glucose level has to be regularly determined, e.g. by making use of a blood glucose measurement device (BGM). Depending on the measured data and a determined blood glucose concentration the patient may then individually select a dose of a medicament which is to be administered, e.g. by way of injection.

There exists a large variety of medical devices for analysing and treating patients for diagnostic and/or therapeutic purpose. Such medical devices are sometimes rather fragile and sensitive to mechanical impact.

In general, medical devices may comprise a variety of sensitive components which require sufficient protection against external hazards. Portable or mobile medical devices may also comprise a large variety of electronic components, by way of which various functionalities of the device can be configured, controlled and conducted. Additionally, such devices may comprise various input and/or output means, such like a display, operating buttons and knobs, regulators, dose dials and so on.

Moreover, medical devices may also comprise a storage module by way of which repeated use of the medical device can be monitored and logged. Also, medical devices may comprise a communication module, such like an interface, by way of which treatment-related or device-configuration-related data can be exchanged with additional devices, such like personal computers or smartphones.

The various components of such portable medical devices may be rather susceptible to mechanical impact and may affect the general operability of such devices when exposed to mechanical impact above a certain threshold.

It is therefore an object of the present invention to provide an improved housing for a medical device to enhance robustness and susceptibility of the device and its components against mechanical impact. It is a particular aim to provide an impact- or shock-absorbing functionality and to provide further a well-defined impact- or crash-behaviour of the medical device. These improvements regarding impact protection should be rather simple and cost-efficient to realize.

SUMMARY

In a first aspect a housing for a medical device is provided which comprises a body to receive at least one device component. The body serves as an outer shell of the medical device and may even constitute the housing of the medical device. The body is flexibly deformable in response to mechanical impact above a predefined threshold. This way, the body of the housing or the housing itself may absorb externally applied forces or impact, which may transfer into a flexible deformation of the body.

The flexible deformation of the body provides a well-defined absorption of kinetic energy and/or momentum, which is typically set free in the event of an impact, e.g. when the medical device drops down to a ground surface and hits the same. By providing a flexibly deformable body, the housing serves as an impact- or crash-protection means adapted to absorb externally applied forces which may act on the device in the event of an impact. This way, at least some of the device components can be effectively protected against mechanical impact and respective externally applied mechanical forces.

In an impact- or crash-scenario a magnitude and/or duration of the mechanical impact present on the at least one device component can be effectively reduced compared to conventional medical devices featuring a rather stiff and rigid housing, which in an impact-event may either tend to break, to crack or to transfer an incident impact in a rather unaltered way across its housing.

Moreover, by providing a flexibly deformable body of a housing, the housing may remain substantially intact even when becoming subject to mechanical impact. Generally, a flexibly deformable body features a reduced tendency to breakage or crack formation.

The flexibly deformable body may change its shape and/or geometry under the effect of an impact or comparable mechanical load. Depending on the type of material the body is made of, the change in shape of the body may be permanent or temporary.

In a preferred embodiment, the body of the housing is either elastically or plastically deformable in response to mechanical impact above a predefined threshold. Here, either the entire body or at least a portion thereof is elastically or plastically deformable. It is even conceivable, that particular portions of the body are elastically deformable whereas other portions of the body are substantially plastically deformable. Since plastically and flexibly deformable portions of the body do not provide restoring forces that may transfer the body into an initial shape, an impact-event may lead to a durable deformation of the body, which is detectable, either visually or haptically by a user of the device.

Hence, with a plastically and flexibly deformable body, the housing itself is immediately indicative that it has been subject to a potentially hazardous and/or damaging event. In this case, also the outer appearance of the medical device may be seriously affected, thereby encouraging the end user to bring the medical device to a maintenance service.

In contrast to that, an elastically deformable housing or an elastically deformable portion of the housing may provide a particular restoring force immediately after an impact- or crash-event, leaving the outer appearance of the device substantially untouched.

In preferred embodiments it is even conceivable, that the body features elastically as well as plastically deformable properties. For instance, the body at least in sections may provide an elastically deformable behaviour as long as the mechanical impact is below a predefined threshold. Above said threshold, the flexibly deformable behaviour of the body or sections thereof may be governed by a plastic deformation, thereby indicating, that the device and/or at least components thereof may be damaged or may require at least a check-up. Here, an impact-threshold can be selected in such a way, that impact- or crash-scenarios below said threshold do normally not induce malfunctions or damages of the device and/or of its components. However, only above said threshold, where impact-induced damages or male functions may occur, the body may exhibit a plastic and hence durable deformation behaviour.

In a further embodiment, the body comprises at least one predetermined buckling or bending portion. In this way, a predetermined bending or buckling behaviour of the body and the housing can be provided. In particular, the body may comprise different portions made of different materials, which react in different and well-defined ways to mechanical impact or comparable externally applied forces. Depending on the device, its general functionality, its construction and/or arrangement of various device components, selected portions of the body may feature a rather stiff and rigid response to externally applied forces whereas other portions may exhibit a comparatively flexible and deformable behaviour.

This way, the flexibly deformable behaviour of the body and/or of the housing can be locally adapted to various components of the medical device. By having a zone of increased flexible deformation, a kind of crash- or impact-absorption zone of the body can be provided whereas other portions of the body featuring a rather stiff and rigid mechanical behaviour may serve to protect an e.g. elongated structure of a device component located therein. If the medical device for instance comprises a vitreous cartridge filled with a medicament, the particular portion of the housing which receives and encloses the cartridge should provide only a limited flexible deformation behaviour for not exhibiting the cartridge located therein to mechanical impact or shear forces.

According to another embodiment, the body at least in sections comprises a bendable or deformable polymeric material. Moreover, the entire body or sections thereof may be made of a polymeric material. The body may comprise also elastomeric materials predominately providing elastic deformation. Among a plurality of elastic polymeric materials numerous dimensionally stable materials, such as polycarbonate, grilamid TR-90, thermoplastic polyurethane (TPU), cellulose acetate, silicone and/or mixtures thereof may be used. Other, comparatively soft materials to form the body may comprise various thermoplastic elastomers (TPE), silicone, ethylene propylene diene monomer rubber (EPDM rubber) and/or mixtures thereof.

The particular choice and constitution of the materials the body is made of may depend on the generic properties and demands of the medical device. Flexible deformation of the body may be therefore individually adapted and may vary among different medical devices and respective housings.

In a further embodiment, the body of the housing comprises at least in sections a multilayer structure. It is even conceivable, that the entire body comprises a multilayer structure. A multilayer structure comprises at least a first layer and a second layer, wherein first and second layers comprise different mechanical properties regarding mechanical stiffness or rigidity. Consequently, first and second layers exhibit different degrees of mechanical resistance against mechanical impact. In particular, first and second layers exhibit different flexible deformation behaviours.

By combining at least two layers of different materials, the flexible and deformable behaviour of the body can be individually adapted and modified according to the mechanical demands of the respective medical device. In particular, the first layer, which may face inwardly may be rather stiff and/or rigid. Hence, said layer may provide a comparatively high threshold regarding mechanical impact until a flexible deformation occurs. The second layer, e.g. facing outwardly and being interconnected or bonded to the first layer, may feature a comparatively elastic and soft behaviour and may therefore tend to deform substantially elastically in response to mechanical impact below a deformation threshold of the first layer.

In this way, the first and outer layer may provide mechanical damping and/or a suspension effect whereas the second layer may provide a well-defined stiffness and rigidity to the body and/or to the housing. Only in the event of mechanical impact above a damaging threshold, the first layer of the body may become subject to an e.g. plastic deformation.

In a further embodiment, the first layer comprises a sheet metal whereas the second layer, which is preferably bonded with the first layer, comprises a polymeric material exhibiting a larger elasticity compared to the material the first layer is made of. Instead of a sheet metal, which may exhibit plastic deformation behaviour when getting subject to mechanical impact above the predefined threshold, also comparable polymeric materials exhibiting a geometrically stable geometry and a comparative deformation behaviour may be used as a first layer.

Moreover, the multilayer structure is not limited to only two layers but may comprise even three or more layers of variable and different thickness which may further comprise different materials.

In a further embodiment, the polymeric material of the second layer entirely encloses or substantially encapsulates the first layer. This way, the first layer does substantially not contribute to the outer appearance of the housing of the medical device. Instead, the second layer may serve as a protective, e.g. shock- or impact-absorbing cover or coating. In general, it is conceivable, that at least one layer of a multilayer structure of the body is manufactured by way of one- or multi-component injection molding and/or by coating.

According to a further embodiment, the polymeric material of the body and/or of at least one layer of the body is made of a material being initially liquid but being curable, e.g. by means of UV-radiation. Hence, the body and/or at least one layer thereof may be formed by immersing a pre-formed body into a vessel filled with a substantially liquid or viscous polymeric material and by curing the coated polymeric material by means of UV-radiation thereafter. After curing, the polymeric material, such like silicone, may be geometrically stable but may still exhibit an elastic or plastic flexible deformation behaviour.

In another aspect, the body of the housing further comprises at least one fastening assembly to attach the at least one device component to the body. Typically, the body forms or comprises sidewalls of the housing of the medical device or of a comparable support structure, to which at least one or several device components can be fastened and/or assembled. Since the body itself is flexibly deformable, the device components individually assembled to the body can be effectively damped against mechanical impact since the interconnecting body inherently provides a shock- or impact absorbing functionality.

Moreover, when the body is flexibly deformable in a portion between selected device components, said components may become subject to a relative movement in the event of an impact. This way and in the event of a mechanical impact, the body may provide an evasive movement of device components relative to each other, thereby protecting particular device components against undue mechanical loads.

In a further aspect, the fastening assembly comprises at least one receptacle to receive a correspondingly shaped insert. Preferably, it is the body of the housing which comprises the receptacle to receive the insert of the device component. However, it is also conceivable, that the insert is provided by the body of the housing, whereas the device component comprises a correspondingly shaped receptacle.

Moreover, an intermediate space between the receptacle and the insert of the fastening assembly is substantially filled or lined with an elastic damping member. This way, the insert of the device component or of the housing is only in indirect and damped mechanical engagement with the receptacle of the body or device component. In effect, the elastic damping member serves to provide a shock-absorbing fastening of the at least one device component to the body of the housing of the medical device. In the event of an impact, mechanical load present on the housing and the body may be transferred to respective device components only in an attenuated or damped way.

In a further preferred embodiment, insert and receptacle of the fastening assembly are adapted to positively engage. Depending on the manufacturing of the body, the positive engagement of insert and receptacle may be established even during manufacturing of the body. Hence, the insert of the medical device component may be positioned at a predefined location in a pre-form or mold and may then be overmolded or encapsulated by the material of the body during manufacture thereof.

Otherwise, insert and receptacle of device component and body may be manufactured separately and may be mutually assembled in a separate assembling step.

In another aspect, the invention also relates to a medical device comprising at least one device component and a housing as described above.

Moreover, in preferred embodiments, the medical device comprises a drug delivery device, in particular an injection device, such like a pen-type injector. Alternatively, the medical device may comprise an analysis device, such like a blood glucose monitoring device.

Moreover and according to a further embodiment, the drug delivery device, in particular the injection device further comprises at least one cartridge, an ampoule or carpule which may comprise a vitreous container filled with a medicament to be administered or to be delivered to a patient, preferably by way of injection.

In still another and independent aspect the invention relates to a method of manufacturing a housing of a medical device. Said method comprises the steps of arranging at least one device component at a predefined location of a preform or mold and to mold a body of the housing at least partially around the device component and/or around an insert thereof to establish a positive engagement of the body and the device component. Here, it is of particular benefit when the device component comprises an appendix or protrusion to be at least partially embedded in the bulk of the body during a molding process thereof.

It is of particular benefit when the device component comprises an insert which is at least partially wrapped or enclosed with a deformable material thereby forming an elastic damping member. Then, the insert of the device will not get in direct but only in a mechanically damped or suspended contact with the body of the housing.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(107-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2 (SEQ ID NO: 1).

Exendin-4 derivatives are for example selected from the following list of compounds:

```
H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39),
``` wherein the group -Lys6-NH2 (SEQ ID NO: 50)may be bound to the C-terminus of the Exendin-4 derivative;

or an Exendin-4 derivative of the sequence

```
des Pro36 Exendin-4(1-39)-Lys6-NH2 (AVE0010),

H-(Lys)6-des Pro36 [Asp28] Exendin-4(1-39)-
Lys6-NH2, des Asp28 Pro36, Pro37, Pro38Exendin-4(1-39)-NH2, H-(Lys)6-des Pro36, Pro38 [Asp28]
Exendin-4(1-39)-NH2, H-Asn-(Glu)5des Pro36, Pro37, Pro38 [Asp28]
Exendin-4(1-39)-NH2, des Pro36, Pro37, Pro38 [Asp28] Exendin-4
(1-39)-(Lys)6-NH2, H-(Lys)6-des Pro36, Pro37, Pro38 [Asp28]
Exendin-4(1-39)-(Lys)6-NH2, H-Asn-(Glu)5-des Pro36, Pro37, Pro38 [Asp28]
Exendin-4(1-39)-(Lys)6-NH2, H-(Lys)6-des Pro36 [Trp(O2)25, Asp28]
Exendin-4(1-39)-Lys6-NH2, H-des Asp28 Pro36, Pro37, Pro38 [Trp(O2)25]
Exendin-4(1-39)-NH2, H-(Lys)6-des Pro36, Pro37, Pro38 [Trp(O2)25, Asp28]
Exendin-4(1-39)-NH2, H-Asn-(Glu)5-des Pro36, Pro37, Pro38 [Trp(O2)25,
Asp28] Exendin-4(1-39)-NH2, des Pro36, Pro37, Pro38 [Trp(O2)25, Asp28]
Exendin-4(1-39)-(Lys)6-NH2, H-(Lys)6-des Pro36, Pro37, Pro38 [Trp(O2)25,
Asp28] Exendin-4(1-39)-(Lys)6-NH2, H-Asn-(Glu)5-des Pro36, Pro37, Pro38 [Trp(O2)25,
Asp28] Exendin-4(1-39)-(Lys)6-NH2, H-(Lys)6-des Pro36 [Met(O)14, Asp28]
Exendin-4(1-39)-Lys6-NH2, des Met(O)14 Asp28 Pro36, Pro37, Pro38
Exendin-4(1-39)-NH2, H-(Lys)6-desPro36, Pro37, Pro38 [Met(O)14, Asp28]
Exendin-4(1-39)-NH2, H-Asn-(Glu)5-des Pro36, Pro37, Pro38 [Met(O)14,
Asp28] Exendin-4(1-39)-NH2, des Pro36, Pro37, Pro38 [Met(O)14, Asp28]
Exendin-4(1-39)-(Lys)6-NH2, H-(Lys)6-des Pro36, Pro37, Pro38 [Met(O)14, Asp28]
Exendin-4(1-39)-(Lys)6-NH2, H-Asn-(Glu)5 des Pro36, Pro37, Pro38 [Met(O)14,
Asp28] Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25] Exendin-4(1-39)-NH2, H-(Lys)6-des Pro36, Pro37, Pro38 [Met(O)14,
Asp28] Exendin-4(1-39)-NH2, H-Asn-(Glu)5-des Pro36, Pro37, Pro38 [Met(O)14,
Trp(O2)25, Asp28] Exendin-4(1-39)-NH2, des Pro36, Pro37, Pro38 [Met(O)14, Trp(O2)25,
Asp28] Exendin-4(1-39)-(Lys)6-NH2, H-(Lys)6-des Pro36, Pro37, Pro38 [Met(O)14,
Trp(O2)25, Asp28] Exendin-4(S1-39)-(Lys)6-NH2, H-Asn-(Glu)5-des Pro36, Pro37, Pro38 [Met(O)14,
Trp(O2)25, Asp28] Exendin-4(1-39)-(Lys)6-NH2;
``` or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which.

DETAILED DESCRIPTION

Figure 1:
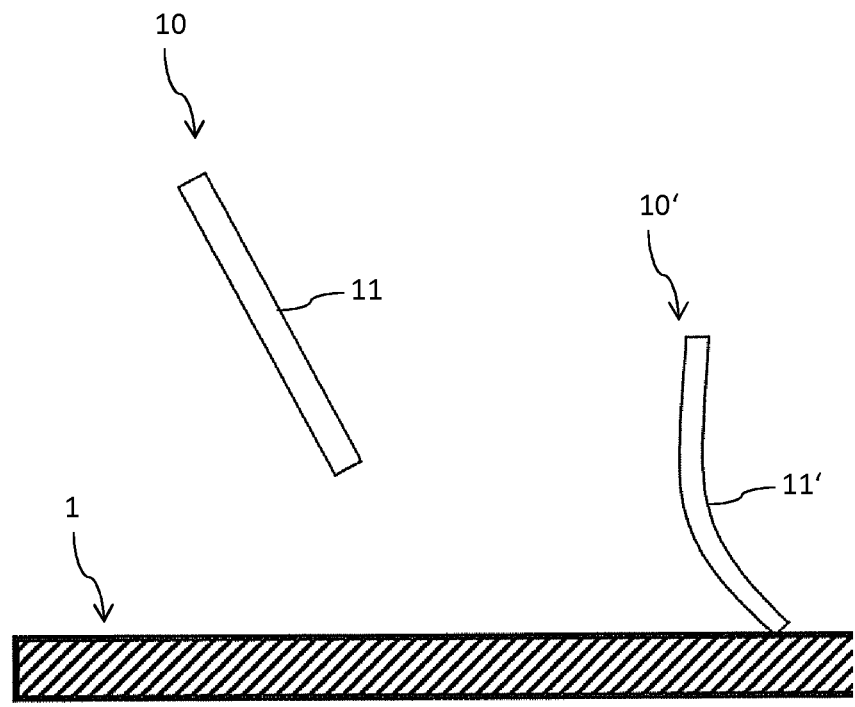
FIG. 1 schematically illustrates the medical device in a sequence prior and after an impact-event, FIG. 2 schematically illustrates a fastening assembly to fasten at least one device component to the body of the housing of the medical device, FIG. 3a schematically illustrates a housing of a drug delivery device comprising a deformation zone prior to an impact-event

In FIG. 1 a simplified schematic illustration of a medical device is provided prior and after an impact event. The medical device comprises a housing 10 of elongated or rod-like shape. The housing 10 and the respective medical device may for instance comprise a drug delivery device, such like a pen-type injector.

As indicated on the right hand side of FIG. 1, the housing 10 comprises a body 11, which undergoes a flexible deformation and a respective modification of its geometric shape when the housing 10 hits a ground surface 1. In the event of falling down to a ground surface 1, e.g. when hitting the ground surface 1 under the effect of gravity, the housing 10 and its body 11 may experience mechanic load and/or impact above a predefined threshold leaving to a flexible deformation of the body 11' and the housing 10', by way of which impact- or shock-energy can be transferred into a respective geometric deformation of the housing 10' and the body 11'. This way, an impact-induced release of mechanical energy can be at least partially absorbed by the body 11'. As a consequence, particular components 14 of the medical device, which are not explicitly illustrated here, can be effectively protected against mechanical impact.

Hence, a well-defined, or predetermined flexible deformation behaviour of the housing 10 of the medical device can be provided, by way of which rather sensitive device components can be effectively protected against mechanical impact.

Such device components may comprise for instance a display element, a communication module or a cartridge filled with a medicament. By providing a shock- or impact-absorbing functionality, such device components 14 can be effectively protected and may be of further use, even when the device may be destroyed or may be substantially inoperable due to the impact-event. By protecting electronic device components, such like a communication module, a storage module, a processing module and/or a display, medical treatment related data or comparable information may still be retrieved and read out from the device. For instance, an application history of the medical device may still be retrieved even when other components of the device, e.g. an injection mechanism became substantially inoperable.

The entire body of the housing may be coated or surrounded by a flexibly deformable material, in particular by a particular polymeric material in a single- or multilayer configuration. However, the body 11 and the housing 10 may comprise at least one or several through openings in order to provide access to particular device components, such like operating means, which may be implemented mechanically or electronically. Such operating means, e.g. in form of buttons, dials or the like may also exhibit a flexible deformation behaviour. Also display elements, which may be positioned in or which may extend through at least one opening of the body may exhibit and provide a particular flexibility. Such flexible display elements may be particularly based on organic light emitting diodes (OLED).

Figure 3A:
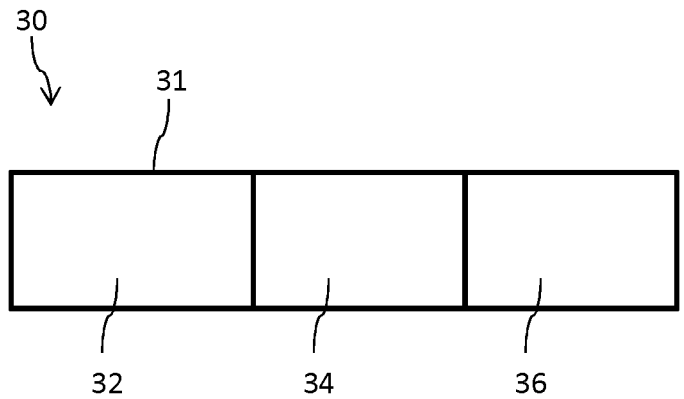
FIG. 3b shows the housing according to FIG. 3a after an impact-event and FIG. 4 schematically illustrates a multilayer structure of a housing of a medical device.
Figure 3B:
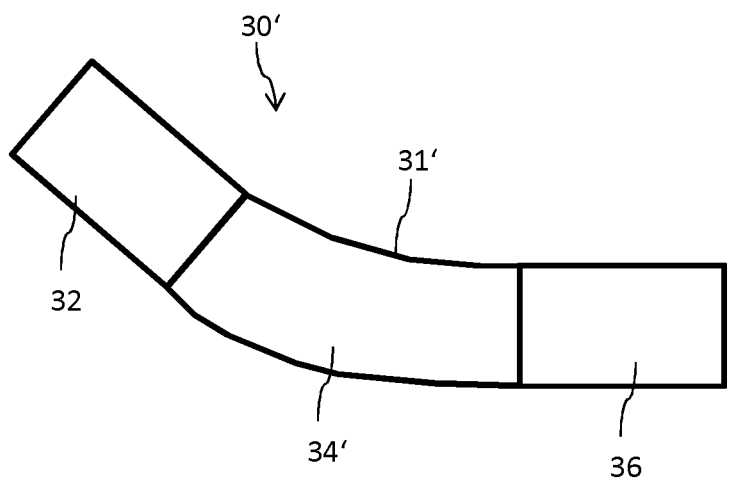

As further indicated for instance in FIG. 3a, the housing 30 of the medical device may comprise a body 31 featuring a first end portion 32 and a second end portion 36 located at different opposite end sections of the body 31. The two end portions 32, 36 are interconnected by a middle portion 34 extending between the two end portions 32, 36. Here, at least the middle portion 34 exhibits a well-defined flexible deformation behaviour in response to mechanical impact. The middle portion 34 therefore serves as a kind of buckling or bending portion of the housing 30. As illustrated in FIG. 3b the middle portion 34' may plastically deformed when becoming subject to externally applied mechanical loads or impact.

Alternative to the illustration of a geometrically modified housing 30' according to FIG. 3b it is also conceivable, that the middle portion 34 is elastically deformable, thereby restoring the initial shape and geometry of the housing 30 even after an impact-event has occurred.

Figure 4:
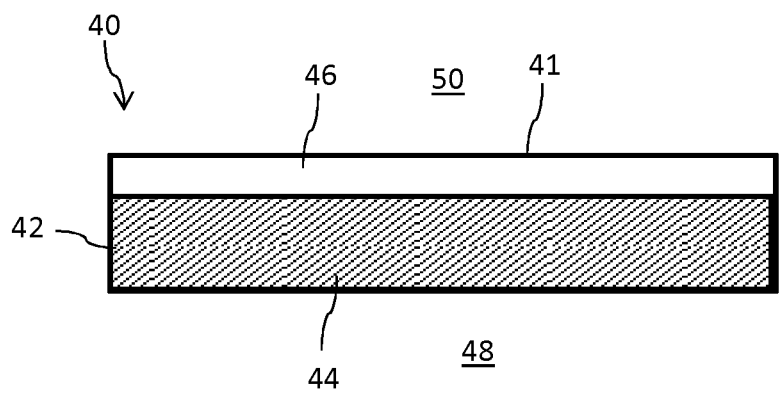

In FIG. 4, another housing 40 featuring a body 41 is shown only in sections. Here, a sidewall 42 of the body 41 is shown in cross section which comprises a multilayer structure with an outer layer 44 and an inner layer 46. Accordingly, the outer layer 44 forms an outer surface of the body 41 and faces to the outside 48 whereas the inner layer 46 faces towards an inside 50 of the housing 40 of the medical device. The two layers 44, 46 vary in thickness and may comprise different materials exhibiting different mechanical and flexible deformation behaviour.

The inner layer 46 may for instance comprise a sheet metal being substantially plastically deformable above a comparatively large impact-threshold. The outer layer 44 may comprise a comparatively soft and elastically deformable material, such like a thermoplastic elastomere. This way, the outer layer 44 may provide a shock-absorbing and impact-damping behaviour for impact-events below a predefined threshold whereas the inner layer 46 serves to absorb and to deform under comparatively large mechanical loads and respective mechanical impact.

Figure 2:
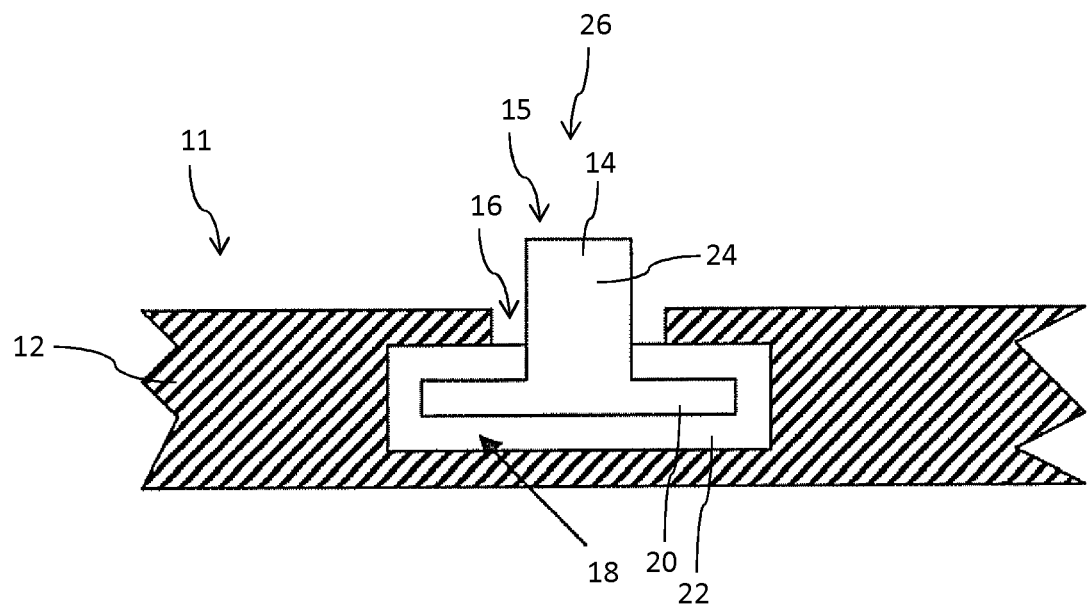

In FIG. 2, a shock-proof or impact-damping fastening assembly 26 is schematically illustrated in cross section, by way of which at least one device component 14 can be attached to the sidewall 12 or to a comparable support structure of the housing 10 of the medical device. The fastening assembly 26 comprises a receptacle 18 located in the sidewall 12 of the body 11. The fastening assembly 26 further comprises an insert 15 provided at an appendix or at a protruding portion of a device component 14. The receptacle 18 is adapted to receive a flange-like portion 20 at a free end of the insert 15 of the device component 14. Hence, the flange-like portion 20 is provided at a free end of a shaft portion 24 of the insert 15 which extends through a neck portion or orifice 16 of the receptacle 18.

The orifice 16 comprises a diameter substantial larger than the shaft portion 24 of the device component 14 but being smaller than the radial extension of the flange-like portion 20 of the device component 14. This way, the fastening assembly 26 provides a positive engagement of the device component 14 and the receptacle 18 of the sidewall 12 of the body 11.

An intermediate space between the shaft portion 24, the flange-like portion 20 and the sidewalls of the receptacle 18 is preferably filled or lined with an elastic damping member 22. This way, a shock-absorbing suspension-like fastening of the device component 14 and the body 11 can be attained. The device component 14, its shaft portion 24 as well as the flange-like portion 20 may comprise a rather solid or rigid constitution. By means of the elastic damping member 22, mechanical impact and mechanical loads in general impinging on the body 11 will be transferred to the device component 14 in a damped and attenuated way.

The positive engagement of the device component 14 and the receptacle 18 can be attained by positioning the device component 14 at a particular location in a preform or in a mold prior to a formation of the body 11. The flange-like portion 20 may be wrapped and/or coated with the elastic member 22 and in a final formation process the body 11 may be molded, e.g. injection molded around the flange-like portion 20 of the insert 15 of the device component 14.

Other methods of assembly may include, that the flange-like portion 20 is of non-circular shape and that the orifice 16 comprises a corresponding shape in a selected direction. Then, the shaft 24 of the device component 14 may enter and extend through the orifice 16 with the flange-like portion in a predefined orientation. When the flange-like portion 20 is located inside the radially widened receptacle 18 it may be rotated and turned around with the shaft portion 24 as an axis of rotation, thereby establishing a positive-interlocking configuration as illustrated in FIG. 2.

The invention claimed is:

1. An elongate housing of a pen-type medical device comprising a body to receive at least one device component therein, wherein the at least one device component is arranged inside the body, and wherein the at least one device component comprises an electronic display, a cartridge filled with a medicament, or both,
   wherein the body forms a sidewall of the pen-type medical device and defines an outer surface of the pen-type medical device,
   wherein the body is flexibly deformable in response to mechanical impact above a predefined threshold, and
   wherein the body has a longitudinal axis and comprises:
      a first longitudinal end portion and a second longitudinal end portion located at opposite ends of the body; and
      a middle portion extending longitudinally between and interconnecting the first longitudinal end portion and the second longitudinal end portion, wherein the body is, at least in a cross-section of the body that is transverse to the longitudinal axis of the body at the middle portion, made of one or more bendable or deformable polymeric materials, wherein the entire middle portion is a predefined buckling or bending portion of the body configured to deform plastically or elastically in response to mechanical impact above the predefined threshold at one or both of the first longitudinal end portion and the second longitudinal end portion of the body, and wherein the middle portion is a zone of the body having a flexible deformation capability larger than a flexible deformation capability of the first longitudinal end portion and the second longitudinal end portion.

2. The elongate housing according to claim 1, wherein the body is elastically or plastically deformable.

3. The elongate housing according to claim 1, wherein the one or more bendable or deformable polymeric materials is UV-curable or is UV-cured.

4. The elongate housing according to claim 1, wherein the middle portion of the body, at least in one crosswise section with respect to a longitudinal axis of the elongate housing, is made of the bendable or deformable polymeric material.

5. The elongate housing according to claim 1, wherein the body is configured to transfer at least a portion of an impact energy or shock energy from a mechanical impact at the first longitudinal end portion or the second longitudinal end portion into deformation of the predefined buckling or bending portion.

6. The elongate housing according to claim 1, wherein the body comprises at least one fastening assembly, and wherein the at least one device component is attached to the body by the at least one fastening assembly.

7. The elongate housing according to claim 1, wherein the body comprises at least a first layer having a mechanical stiffness or rigidity and a second layer having a different mechanical stiffness or rigidity than that of the first layer.

8. The elongate housing according to claim 7, wherein the first layer comprises a sheet metal and wherein the second layer comprises a polymeric material.

9. The elongate housing according to claim 8, wherein the polymeric material of the second layer entirely encloses the first layer.

10. The elongate housing according to claim 1 further comprising at least one fastening assembly to attach the at least one device component to the body.

11. The elongate housing according to claim 10, wherein the at least one fastening assembly comprises at least one receptacle to receive a correspondingly shaped insert, and wherein an intermediate space between the at least one receptacle and the insert is substantially filled or lined with an elastic damping member.

12. The elongate housing according to claim 11, wherein the insert and the at least one receptacle are positively engageable by interlocking or are interlocked with each other.

13. A pen-type injection device comprising a cartridge filled with a medicament and comprising an elongate housing, the elongate housing comprising:
a body to receive the cartridge therein,
wherein the body forms a sidewall of the pen-type injection device and defines an outer surface of the pen-type injection device,
wherein the body is flexibly deformable in response to mechanical impact above a predefined threshold, and
wherein the body has a longitudinal axis and comprises:
a first longitudinal end portion and a second longitudinal end portion located at opposite ends of the body; and
a middle portion extending longitudinally between and interconnecting the first longitudinal end portion and the second longitudinal end portion, wherein the body is, at least in a cross-section of the body that is transverse to the longitudinal axis of the body at the middle portion, made of one or more bendable or deformable polymeric materials, wherein the entire middle portion is a predefined buckling or bending portion of the body configured to deform plastically or elastically in response to mechanical impact above the predefined threshold at one or both of the first longitudinal end portion and the second longitudinal end portion of the body, and wherein the middle portion is a zone of the body having a flexible deformation capability larger than a flexible deformation capability of the first longitudinal end portion and the second longitudinal end portion.

14. An elongate housing of a pen-type medical device comprising a body configured to receive or to accommodate a cartridge filled with a liquid medicament that is intended for administration into biological tissue by way of injection,
wherein the body forms a sidewall of the pen-type medical device and defines an outer surface of the pen-type medical device,
wherein the body is flexibly deformable in response to mechanical impact above a predefined threshold, and
wherein the body has a longitudinal axis and comprises:
a first longitudinal end portion and a second longitudinal end portion located at opposite ends of the body; and
a middle portion extending longitudinally between and interconnecting the first longitudinal end portion and the second longitudinal end portion, wherein the body is, at least in a cross-section of the body that is transverse to the longitudinal axis of the body at the middle portion, made of one or more bendable or deformable polymeric materials, wherein the entire middle portion is a predefined buckling or bending portion of the body configured to deform plastically or elastically in response to mechanical impact above the predefined threshold at one or both of the first longitudinal end portion and the second longitudinal end portion of the body, and wherein the middle portion is a zone of the body having a flexible deformation capability larger than a flexible deformation capability of the first longitudinal end portion and the second longitudinal end portion.

15. The elongate housing according to claim 14, wherein the pen-type medical device is an injection device for administering the liquid medicament by way of injection.

* * * * *

UNITED STATES PATENT AND TRADEMARK OFFICE
CERTIFICATE OF CORRECTION

Page 1 of 2

PATENT NO. : 10,973,981 B2
APPLICATION NO. : 14/424298
DATED : April 13, 2021
INVENTOR(S) : Michael Jugl et al.

It is certified that error appears in the above-identified patent and that said Letters Patent is hereby corrected as shown below:

On the Title Page

Under item (57), "15 Claims" should read --14 Claims--.

In the Claims

At Column 44, Line 66, through Column 45, Line 2, delete the text from "4. The" through "polymeric material.".

At Column 45, Line 3, replace "5" with --4--.

At Column 45, Line 9, replace "6" with --5--.

At Column 45, Line 13, replace "7" with --6--.

At Column 45, Line 17, replace "8. The elongate housing according to claim 7" with --7. The elongate housing according to claim 6--.

At Column 45, Line 20, replace "9. The elongate housing according to claim 8" with --8. The elongate housing according to claim 7--.

At Column 45, Line 23, replace "10" with --9--.

At Column 45, Line 26, replace "11. The elongate housing according to claim 10" with --10. The elongate housing according to claim 9--.

At Column 45, Line 32, replace "12. The elongate housing according to claim 11" with --11. The elongate housing according to claim 10--.

At Column 45, Line 36, replace "13" with --12--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,973,981 B2

At Column 46, Line 16, replace "14" with --13--.

At Column 46, Line 47, replace "15. The elongate housing according to claim 14" with --14. The elongate housing according to claim 13--.

SEQUENCE LISTING

<160> NUMBER OF SEQ ID NOS: 50

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30

Asn Gly Gly Pro Ser Ser Gly Ala Pro Ser
        35                  40

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: IsoAsp

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: IsoAsp

<400> SEQUENCE: 8

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)

<400> SEQUENCE: 9

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 10

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
```

```
                        polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (39)..(44)
<223> OTHER INFORMATION: This region may or may not be present

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 14
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: IsoAsp
<220> FEATURE:
<221> NAME/KEY: SITE
<222> LOCATION: (39)..(44)
<223> OTHER INFORMATION: This region may or may not be present

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: SITE
<222> LOCATION: (39)..(44)
<223> OTHER INFORMATION: This region may or may not be present

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: IsoAsp
<220> FEATURE:
<221> NAME/KEY: SITE
<222> LOCATION: (39)..(44)
<223> OTHER INFORMATION: This region may or may not be present

<400> SEQUENCE: 16

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: SITE
<222> LOCATION: (39)..(44)
<223> OTHER INFORMATION: This region may or may not be present

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp
<220> FEATURE:
<221> NAME/KEY: SITE
<222> LOCATION: (39)..(44)
<223> OTHER INFORMATION: This region may or may not be present

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
```

```
<220> FEATURE:
<221> NAME/KEY: MOD_RES
<222> LOCATION: (25)..(25)
<223> OTHER INFORMATION: Trp(O2)
<220> FEATURE:
<221> NAME/KEY: SITE
<222> LOCATION: (39)..(44)
<223> OTHER INFORMATION: This region may or may not be present

<400> SEQUENCE: 19

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp
<220> FEATURE:
<221> NAME/KEY: SITE
<222> LOCATION: (39)..(44)
<223> OTHER INFORMATION: This region may or may not be present

<400> SEQUENCE: 20

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 22
<211> LENGTH: 50
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
            35                  40                  45

Lys Lys
    50

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
                20                  25                  30

Gly Ala Ser
        35

<210> SEQ ID NO 24
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Ser
            35                  40

<210> SEQ ID NO 25
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Ser
            35                  40
```

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser Lys Lys Lys Lys Lys Lys
        35                  40

<210> SEQ ID NO 27
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 28
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 29
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Trp(O2)

<400> SEQUENCE: 29

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 30
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Ser
        35

<210> SEQ ID NO 31
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Trp(O2)

<400> SEQUENCE: 31

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 32
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Trp(O2)

<400> SEQUENCE: 32

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser 35                  40

<210> SEQ ID NO 33
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Trp(O2)

<400> SEQUENCE: 33

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser Lys Lys Lys Lys Lys Lys
        35                  40

<210> SEQ ID NO 34
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Trp(O2)

<400> SEQUENCE: 34

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 35
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Trp(O2)

<400> SEQUENCE: 35

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 36
<211> LENGTH: 50
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 36

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Gly Glu Gly Thr Phe Thr Ser Asp Leu Ser Lys Gln Glu Glu Glu
1               5                   10                  15

Ala Val Arg Leu Phe Ile Glu Trp Leu Lys Gly Gly Pro Ser Ser Gly
            20                  25                  30

Ala Ser

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 38

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 39
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 39
```

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Ser
            35                  40

<210> SEQ ID NO 40
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)

<400> SEQUENCE: 40

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
                20                  25                  30

Ser Gly Ala Ser Lys Lys Lys Lys Lys Lys
            35                  40

<210> SEQ ID NO 41
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 41

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Ser Lys Lys Lys Lys Lys Lys
            35                  40                  45

<210> SEQ ID NO 42
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 42

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

```
Lys Asp Gly Gly Pro Ser Ser Gly Ala Ser Lys Lys Lys Lys Lys
        35                  40                  45
```

<210> SEQ ID NO 43
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 43

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
        35                  40                  45

Lys Lys
    50
```

<210> SEQ ID NO 44
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 44

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
                20                  25                  30

Gly Ala Ser
        35
```

<210> SEQ ID NO 45
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)

<400> SEQUENCE: 45

```
Lys Lys Lys Lys Lys Lys His Gly Glu Gly Thr Phe Thr Ser Asp Leu
1               5                   10                  15
```

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 46
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 46

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 47
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 47

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser Lys Lys Lys Lys Lys Lys
        35                  40

<210> SEQ ID NO 48
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

```
<400> SEQUENCE: 48

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 49
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 49

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Lys Lys Lys Lys Lys Lys
1               5
```